US009119887B2

(12) United States Patent
Day et al.

(10) Patent No.: US 9,119,887 B2
(45) Date of Patent: Sep. 1, 2015

(54) LOW-DENSITY MAGNESIUM-ALUMINUM-SILICATE (MAS) MICROPARTICLES FOR RADIOTHERAPY AND/OR RADIOIMAGING

(75) Inventors: Delbert E. Day, Rolla, MO (US); Yiyong He, Rolla, MO (US)

(73) Assignee: MO-SCI CORPORATION, Rolla, MO (US)

( * ) Notice: Subject to any disclaimer, the term of this patent is extended or adjusted under 35 U.S.C. 154(b) by 0 days.

(21) Appl. No.: 12/883,813

(22) Filed: Sep. 16, 2010

(65) Prior Publication Data

US 2012/0070371 A1   Mar. 22, 2012

(51) Int. Cl.
*A61K 51/12* (2006.01)
(52) U.S. Cl.
CPC .................................. *A61K 51/1244* (2013.01)
(58) Field of Classification Search
CPC ............................. A61K 51/1244; C01F 7/162
USPC ...................... 424/1.11, 1.25, 1.29, 1.33, 1.61
See application file for complete search history.

(56) References Cited

U.S. PATENT DOCUMENTS

| | | | |
|---|---|---|---|
| 4,339,421 | A | 7/1982 | Schultess et al. |
| 4,789,501 | A | 12/1988 | Day et al. |
| 5,011,677 | A | 4/1991 | Day et al. |
| 5,302,369 | A | 4/1994 | Day et al. |
| 5,320,824 | A | 6/1994 | Brodack et al. |
| 5,560,901 | A | 10/1996 | Brodack et al. |
| 5,611,833 | A | 3/1997 | Brahmbhatt et al. |
| 5,651,956 | A | 7/1997 | Nosco et al. |
| 5,690,908 | A | 11/1997 | Deutsch et al. |
| 6,165,440 | A | 12/2000 | Esenaliev |
| 6,358,531 | B1 | 3/2002 | Day et al. |
| 6,379,648 | B1 | 4/2002 | Day et al. |
| 6,455,024 | B1 | 9/2002 | Glajch et al. |
| 6,589,549 | B2 | 7/2003 | Shih et al. |
| 6,797,704 | B2 | 9/2004 | Leong et al. |
| 7,534,448 | B2 | 5/2009 | Saltzman et al. |
| 7,768,399 | B2 | 8/2010 | Hachmann |
| 2004/0136905 | A1 | 7/2004 | Kent et al. |
| 2004/0197264 | A1 | 10/2004 | Schwarz et al. |
| 2004/0258614 | A1 | 12/2004 | Line et al. |
| 2004/0265350 | A1* | 12/2004 | Sambrook et al. ............ 424/423 |
| 2007/0053830 | A1 | 3/2007 | Peng et al. |
| 2008/0038190 | A1 | 2/2008 | Simpson et al. |
| 2009/0208428 | A1 | 8/2009 | Hill et al. |
| 2010/0055019 | A1 | 3/2010 | Day et al. |
| 2010/0160527 | A1 | 6/2010 | Royer et al. |

FOREIGN PATENT DOCUMENTS

| | | |
|---|---|---|
| CN | 1127093 | 11/2003 |
| CN | 1640498 | 7/2005 |
| CN | 101284161 | 10/2008 |
| CN | 101321542 | 12/2008 |
| EP | 1162626 | 12/2001 |
| JP | 09-165327 | 6/1997 |
| JP | 09-165328 | 6/1997 |
| WO | WO/2005/099363 | 10/2005 |
| WO | WO/2009/064460 | 5/2009 |

OTHER PUBLICATIONS

"Cordierite," http://webmineral.com/data/Cordierite.shtml, published online Nov. 2, 2001.*
Yao, et al., In vitro bioactive characteristics of borate-based glasses with controllable degradation behavior, Journal of the American Ceramic Society, 2007.
Cast steel: Gas Nitriding, Key to Metals, 2009-2010. (not attributed).
Turker and Ozer, Diagnotic Radiopharmaceutical Agents, Journal of Pharmaceutical Science, 29, 145-154, 2004.
Karesh, et al., Radiopharmaceuticals in Nuclear Medicine, nucmedtutorials.com, Apr. 8, 2010.
Saatchi and Hafeli, Radiolabeling of Biodegradable Polymeric Microspheres with [99mTc(CO)3]+ and in Vivo Biodistribution Evaluation using MicroSPECT/CT Imaging, Bioconjugate Chem., 2009, 20, 1209-1217.
Rahman, et al., Preparation and Bioactive Characteristics of Porous Borate Glass Substrates, Ceramic Engineering and Science Proceedings, vol. 26, Issue 6, Ch. 1, 2005.
Harley, et al., the Distribution of H20 between Cordierite and Granitic Melt: H2O Incorporation in Cordierite and its Application to High-grade Metamorphism and Custal Anatexis, Journal of Petrology, vol. 42, No. 9, pp. 1595-1620, 2001.
Hamami, SPECT/CT with 99mTc-MAA in Radioembolization with 90Y Microspheres in Patients with Hepatocellular Cancer, Journal of Nuclear Medicine, vol. 50, No. 5, pp. 688-692, 2009.
Yao, et al., In vitro bioactive characteristics of borate-based glasses with controllable degradation behavior, Journal of the American Ceramic Society, 2007.
Christoffersen, et al., Effects of strontium ions on growth and dissolution of hydroxyapatite and on bone mineral detection, Bone, Official Journal of the International Bone and Mineral Society, vol. 20, Issue 1, pp. 47-54, Jan. 1997.
Dedhiya, et al., Mechanism for the Retardation of the Acid Dissolution Rate of Hydroxyapatite by Strontium, Journal of Dental Research, 1973; 52; 1097.
Pan, et al., Strontium borate glass: potential biomaterial for bone regeneration; Journal of the Royal Society; dol: 10.1098/rsif.2009.0504; Dec. 23, 2009.
Wu, The study of strontium niobium phosphate glass properties and structure, Master's Thesis, date of defense Jul. 7, 2009.
Sudarsanan and Young, Structure of STrontium Hydroxide Phosphate, Sr5(PO4)3OH, Act Cryst. (1972), B28, 3668.

* cited by examiner

*Primary Examiner* — Michael G Hartley
*Assistant Examiner* — Leah Schlientz

(57) ABSTRACT

This invention relates to low density radioactive magnesium-aluminum-silicate (MAS) microparticles that contain either samarium-yttrium, samarium, or lutetium as medical isotopes for radiotherapy and/or radioimaging.

22 Claims, No Drawings

LOW-DENSITY MAGNESIUM-ALUMINUM-SILICATE (MAS) MICROPARTICLES FOR RADIOTHERAPY AND/OR RADIOIMAGING

CROSS REFERENCE TO RELATED APPLICATIONS

Not applicable.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The present invention relates generally to microspheres useful in the treatment of cancerous and tumor bearing tissue and more particularly to novel low density MAS glass microspheres useful in this treatment.

In the treatment of patients with certain kinds of cancer, methods are known in which radioactive particles are introduced intravascularly in order to trap the radioactive particle at a particular site for its radiation effect.

According to this technique, a small quantity of the radioactive particles are injected into the patient and a diffuse, homogeneous field of radiation within a selected region of the body is achieved by permanent lodgement of the particles in the capillary bed of the proposed area, typically the location of a tumor.

In early applications of this technique, Yttrium oxide powder was suspended in a viscous medium prior to administration. Yttrium was selected for the technique because of its suitable characteristics: it emits nearly 100 percent beta radiation. See, e.g., Nolan, et al., Intravascular Particulate Radioisotope Therapy". The American Surgeon 35: 181-188 (1969) and Grady, et. al., Intra-Arterial Radioisotopes to Treat Cancer", American Surgeon 26: 678-684 (1960). This method is not totally satisfactory, however. Two disadvantages of Yttrium oxide powder are its high density (5.01 gm/cm$^3$ aka 5.01 gm/ml) and irregular particle shape. The high density of pure yttrium oxide powder makes it difficult to keep the particles in suspension in the liquids used to inject them into the body, and accelerates their tendency to settle in the blood stream prior to reaching the desired tumor. The sharp corners and edges of Yttrium oxide particles also irritate surrounding tissue in localized areas, and interfere with the uniform distribution of the radioactive particles in the tumor to be treated.

In later applications, the particles used have been microspheres composed of an ion exchange resin, or crystalline ceramic core, coated with a radioactive isotope such as P-32 or Y-90. Both ion exchange resin and crystalline ceramic microspheres offer the advantage of having a density much lower than that of yttrium oxide particles, and the ion exchange resin offers the additional advantage of being particularly easy to label. See, e.g., Zielinski and Kasprzyk, "Synthesis and Quality Control Testing of $^{32}$P labelled Ion Exchange Resin Microspheres for Radiation Therapy of Hepatic Neoplasms", Int, J. Appl. Radiat. Isot. 34: 1343-1350 (1983). However, whenever a microsphere comprises a core material having an external surface coating which contains the radioactive isotope there is a risk that the radioactive coating may separate from the underlying microsphere core. Any mechanical breakage of the coating can release unwanted radioactivity to other parts of the human body which is highly undesirable. Further disadvantages are presented by the special handling and precautions that are necessary to coat a radioactive isotope onto a crystalline ceramic core, or to label ion exchange resin.

In still another application, microspheres have been prepared comprising a ceramic material and having a radioactive isotope incorporated into the ceramic material. While the release of radioactive isotopes from a radioactive coating into other parts of the human body may be eliminated by incorporating the radioisotopes into ceramic spheres, the latter product form is nevertheless not without its disadvantages. Processing of these ceramic microspheres is complicated because potentially volatile radioactivity must be added to ceramic melts and the microspheres must be produced and sized while radioactive, with concomitant hazards of exposure to personnel and danger of radioactive contamination of facilities.

Certain rare earth aluminosilicate glass microspheres are well known in the art as radiotherapeutics for use in humans. These have been used to irradiate diseased internal organs with beta radiation.

U.S. Pat. Nos. 4,789,501, 5,011,677, and 5,011,797 disclose that Yttrium aluminosilicate (YAS) glass microspheres have been used to treat liver cancer for many years in hundreds of patients. These microspheres lodge predominantly in the tumor vascular bed (capillary) and deliver effective, high doses of radiation.

Another rare earth aluminosilicate, Samarium aluminosilicate glass microspheres, have also been used to irradiate the organs of mammals. E. M. Erbe and D. E. Day, "Properties of $Sm_2O_3$—$Al_2O_3$_$SiO_2$ Glasses for In vivo Applications", J. Am. Ceram. Soc. 73(9), 1990, 2708-13.

However, there remains a need for a low density microsphere which is useful in the treatment of cancer or tumor bearing tissue, but which will not release a radioactive coating or isotope into remote parts of the body of the patient after administration, will not require any technicians to handle any radioactive materials during the formation and spheroidization of the microsphere and which have a density which will permit the microspheres to be suspended in a fluid suitable for injection into a human.

BRIEF SUMMARY OF THE INVENTION

In a preferred embodiment there is provided a method of administering radioactive magnesium-alumina-silicate glass microparticles to a patient in need thereof, comprising delivering by catheter to an artery that feeds an organ or a tumor of a patient a composition comprising radioactive magnesium-alumina-silicate glass microparticles having a density of about 3.0 g/ml or less, and that contain at least one medical isotope selected from the group consisting of samarium-153, yttrium-90, and lutetium-177, and a physiologically acceptable carrier, wherein the magnesium-alumina-silicate glass microparticles are about 20 to about 200 um in diameter.

In another preferred embodiment, there is provided wherein the method further comprises wherein the at least one medical isotope is a combination of samarium-153 and yttrium-90, or alternatively, wherein the at least one medical isotope is lutetium-177, or alternatively wherein the at least one medical isotope is samarium-153.

In a preferred embodiment, the microparticle has a size range from about 25 to 38 um, a density of 2.8 g/ml, and either a $^{177}$Lu (Lutetium-177) specific activity of 32 mCi per $10^7$ microparticles for imaging, a $^{90}$Y (Yttrium-90) specific activity of 162 mCi per $10^7$ microparticles for therapy, a$^{153}$Sm (Samarium-153) specific activity of 12 mCi per 250,000 microparticles for imaging, or combinations of Lutetium-Yttrium, Samarium-Yttrium, or combinations of other radio-isotopes.

In a preferred embodiment, the magnesium-alumina-silicate glass is a composition having an approximate chemical formula of $2(MgO)-2(Al_2O_3)-5(SiO_2)$.

In another preferred aspect, the aluminum-magnesium-silica glass core has the approximate weight percent ranges of magnesium-alumina-silicate glass comprising: MgO 8-14%; $Al_2O_3$ 32-35%; and $SiO_2$ 47-52%.

In another preferred embodiment, there is provided a method of obtaining a radiologic image of a patient's organ, comprising administering by catheter to an artery that feeds the organ of the patient a composition containing radioactive magnesium-alumina-silicate glass microparticles that have a density of about 3.0 g/ml or less contain samarium-153 or lutetium-177 as the medical isotope in a physiologically acceptable carrier, and obtaining the radiologic image of the patient's liver by capturing the radiation emitted by the samarium-153 or lutetium-177 using a suitable radionuclide imaging technique.

Preferably, the radionuclide imaging technique is single photon emission computed tomography (SPECT).

In another preferred embodiment, there is provided a method of administering radioactive magnesium-alumina-silicate glass microparticles that contain both samarium-153 as a radiodiagnostic medical isotope and yttrium-90 as a radiotherapeutic medical isotope to a patient in need thereof, comprising delivering by catheter to the organ artery of a patient a composition comprising radioactive magnesium-alumina-silicate glass microparticles that have a density of 3.0 g/ml or less and that contain a radiodiagnostic amount of samarium-153 and a radiotherapeutic amount of yttrium-90, and a physiologically acceptable carrier, wherein the magnesium-alumina-silicate glass microparticles are about 20 to about 200 um in diameter

DETAILED DESCRIPTION OF THE INVENTION

In accordance with the present invention, novel low density MAS microspheres and methods have been devised for use in the therapy and/or imaging of certain cancers and tumor bearing tissue. The invention contemplates a glass material having a stable element which can be activated by neutron irradiation to produce a beta or gamma radiation emitting isotope distributed substantially uniformly throughout the glass. Thus, these novel low density microspheres may be manufactured and sized before radioactivity is induced, thereby avoiding the necessity of either bonding a radioelement onto the microsphere surface, or adding radioisotopes to a high temperature melt and spheroidizing and sizing the particles while intensely radioactive.

Mas Glass

In a preferred embodiment, the microparticle is manufactured from a Magnesia-Alumina-Silicate-type glass. In a preferred aspect, the magnesia-alumina-silica glass core has the approximate weight percent ranges of magnesia-alumina-silica comprising:
MgO 8-14%;
$Al_2O_3$ 32-35%; and
$SiO_2$ 47-52%.

Cordierite, a magnesium aluminosilicate, is known for it's excellent thermal properties in industrial applications, and has also been reported to be useful as an antacid when administered as a fine powder, creating a gel-like coating and decomposing safely into magnesium products. Cordierite's chemical composition has been reported as MgO 8-14%; $Al_2O_3$ 32-35%; $SiO_2$ 47-52%; sometimes FeO 0-9%; $K_2O$ 0.02-0.12%; $Na_2O$ 0.9-0.14%. As contemplated herein, the MAS glass will be substantially devoid of impurities.

Manufacture of Microspheres

The microspheres of the present invention may be prepared from a homogenous mixture of powders (i.e., the batch) that is melted to form the desired glass composition. The exact chemical compounds or raw materials used for the batch are not critical so long as they provide the necessary oxides in the correct proportion for the melt composition being prepared. For instance, if a SmY-MAS glass is being made, then samaria, yttria, magnesia, alumina, and silica powders could be used as the batch raw materials. The purity of each raw material is preferably greater than 99.9%. Note that the raw materials must be free of any neutron activatable impurities that would produce undesirable radiation.

After either dry or wet mixing of the powders to achieve a homogeneous mixture, the mixture may be placed in a platinum crucible for melting. The crucibles containing the powdered batch are then placed in an electric furnace which is heated 1400.degree. to 1600.degree. C., depending upon the composition. In this temperature range, the batch melts to form a liquid which is stirred several times to improve its chemical homogeneity. The melt should remain at 1400.degree. to 1600.degree. C. till all solid material in the batch is totally dissolved, usually 2-8 hours being sufficient. When melting and stirring is complete, the crucible is removed from the furnace and the melt is quickly quenched by pouring the melt onto a cold steel plate or into clean water. This procedure breaks the glass into fragments, which aids and simplifies crushing the glass to a fine powder. The powder is then sized and spheroidized for use.

Microsphere Size

The microspheres of the present invention may be processed to have a size that is appropriate for the therapeutic application. The characteristics of the tissue in which the microspheres will be embedded generally dictate the appropriate size of the microspheres to be employed. Generally, microspheres having a size somewhere within the range of about 20 to 200 micrometers, or in other embodiments from about 5 to about 75 micrometers, are employed for therapeutic applications. In many cases it is preferred that the microspheres have a size somewhere within the range of about 5 to about 50 micrometers. For instance, in the treatment of liver cancer, it is preferred to employ microspheres having a size substantially within the range of about 20 to about 40 micrometers, more preferably 25-38 micrometers; microspheres of this size are small enough to be conveniently delivered to the liver through the hepatic artery but are too large to pass through the capillary bed of the liver.

Where it is desired to use microspheres having a diameter in the range of about 20 to about 40 micrometers, and preferably about 25-38 micrometers, as for example in the treatment of liver cancer, it is preferred that the quenched and broken glass be first crushed to about minus 100 mesh particles using a mortar and pestle. The minus 100 mesh material is then ground using a mechanized mortar and pestle or ball mill, until it passes a 400 mesh sieve.

Spheroidizing

The particles are formed into glass microspheres by introducing the −400 mesh particles into a gas/oxygen flame where they are melted and a spherical liquid droplet is formed by surface tension. The droplets are rapidly cooled before they touch any solid object so that, their spherical shape is retained in the solid product.

Just prior to spheroidizing, the −400 mesh powder is rescreened through a 400 mesh sieve to destroy any large agglomerates that may have formed during storage. The −400 mesh powder is then placed in a vibratory feeder located above the gas/oxygen burner. The powder is slowly vibrated into a vertical ceramic tube which guides the falling powder particles directly into the hot flame of a gas/oxygen burner. Any burner capable of melting −400 mesh particles of the particular glass composition being used is satisfactory. A typical rate for feeding the powder to the flame is 5 to 25 gm/hr with the described apparatus. The flame of the burner is directed into a metal container which catches the small glass beads as they are expelled from the flame. This container can be made of any metal which can withstand the heat of the burner and does not contaminate the glass. The container needs to be large enough so that the molten spheres can cool and become rigid before hitting any solid surface of the catcher container.

Screening

After spheroidization, the glass spheres are collected and rescreened. When the microspheres are intended to be used in the treatment of liver cancer, the fraction less than 30 and greater than 20 micrometers in diameter is recovered since this is the desirable size for use in the human liver. After screening, the −30/+20 microspheres are examined with an optical microscope and are then washed with a weak acid (HCl, for example), filtered, and washed several times with reagent grade acetone. The washed spheres are then heated in a furnace in air to 500.degree.–600.degree. C. for 2-6 hours to destroy any organic material.

The final step is to examine a representative sample of the −30/+20 spheres in a scanning electron microscope to evaluate the size range and shape of the spheres. The quantity of undersize spheres (less than 10 micrometers in diameter) is determined along with the concentration of non-spherical particles. The composition of the spheres can be checked by energy dispersive x-ray analysis to confirm that the composition is correct and that there is an absence of chemical contamination. The glass microspheres are then ready for irradiation and subsequent administration to the patient.

It is preferred that the microspheres be substantially spherical, i.e., there are no sharp edges or points that would cause the microsphere to lodge in a location other than that desired. In this context, elipsoidal and other similarly shaped particles that do not have sharp edges or points would be considered to be substantially spherical in shape. It is also preferred that the microparticles have a solid glass matrix throughout, and are not shells, e.g. microspheres containing a large gas bubble. It is preferred that solid microparticles are more robust, durable, and capable of withstanding radionuclide activation.

In accordance with the present invention, the above processing steps are merely exemplary and do not in any way limit the present invention. Similarly, the present invention is not limited to glass microspheres having a size described above; the size of the microspheres of the present invention may be varied according to the application.

Surface Area, Density

The magnesium aluminosilicate microspheres of the present invention are particularly useful because they have a large surface area, pore structure, and low density. Generally, solid glass microspheres 25 to 20 microns in diameter will have a surface area of 30 $m^2$/g to 50 $m^2$/g. In one embodiment, it is contemplated that the microspheres of the present invention have a median surface area of at least 30 $m^2$/g. In one embodiment, it is contemplated that the microspheres of the present invention have a median surface area of at least 50 $m^2$/g. In another embodiment, it is contemplated that microspheres have a median surface area of at least 100 $m^2$/g. In yet another embodiment, microspheres having a median surface area between about 50 and about 200 $m^2$/g are contemplated as within the scope of the invention.

It is contemplated as within the scope of the invention that the microspheres may be manufactured to have a density that is significantly lower than the 5 g/ml of prior art Yttrium microparticles. In this case, the microparticles of the present invention will preferably have density of 3.0 g/ml or less while maintaining the ability to deliver appropriately high levels of radiation to tissue. In one preferred embodiment, the present invention contemplates microparticles having a size range from about 25-38 um, a density of 3.0 or less, e.g. 2.8 g/ml, and either a $^{177}$Lu (Lutetium-177) specific activity of 32 mCi per $10^7$ microparticles for imaging, a $^{90}$Y (Yttrium-90) specific activity of 162 mCi per $10^7$ microparticles for therapy, a $^{153}$Sm (Samarium-153) specific activity of 12 mCi per 250,000 microparticles for imaging, or combinations of Lutetium-Yttrium, Samarium-Yttrium.

Radioisotopes

In a preferred embodiment of the present invention, the constituent elements of the microspheres are chosen so that when administered to the patient, the microspheres may emit a therapeutic and/or diagnostic intensity and amount of radiation but will not emit a significant amount of unwanted beta or gamma radiation which could have a negative impact on healthy tissue surrounding the cancerous or tumor bearing tissue. In this regard, it is preferred that the constituent elements are MAS-samarium-yttrium, MAS-samarium, and MAS-lutetium.

Diagnostic and/or Therapeutic

In a preferred embodiment of the present invention, the radioisotopes/radionuclides are chosen so that when administered to the patient, the microparticles may emit either diagnostic radiation, therapeutic gamma radiation, or both. Although often many gamma emitters are diagnostic and beta emitters may be therapeutic, this is not necessarily always the case. Accordingly, it is within the scope of the invention to include any radioisotope that may provide diagnostic, therapeutic, or both types of functionality.

The therapeutic radioisotope is chosen to deliver a therapeutic intensity and therapeutic amount of short-range radiation (e.g., a penetration of the tissue on the order of about several millimeters or less) but does not emit a significant amount of unwanted radiation which could have a negative impact on healthy tissue surrounding the cancerous or tumor bearing tissue.

The diagnostic radioisotope is chosen to deliver a diagnostic intensity and diagnostic amount of longer-range radiation (e.g., capable of external detection) but does not emit a significant amount of unwanted radiation.

Patient data such as age, gender, weight, and pre-existing conditions are considered when determining a radiotherapeutic and/or radiodiagnostic profile. Cancer data such as tumor size, tumor type, tumor location, degree of surgical intervention and success, vascular structures within and adjacent to the area being treated, and organ involvement are also considered when determining a radiotherapeutic and/or radiodiagnostic profile.

The radioisotope Yttrium-90, which has a half-life greater than about two days and less than about 30 days is one particularly preferred therapeutic radioisotope which emits therapeutic beta radiation.

For radioimaging, i.e. diagnostic, the radioisotopes Lutetium-177 (177-Lu) is particularly preferred.

The present invention includes wherein the radioisotope is radiopharmaceutical grade and is selected from the group consisting essentially of, but not limited to: Actinium-225, Antimony-127, Arsenic-74, Barium-140, Bismuth-210, Californium-246, Calcium-46, Calcium-47, Carbon-11, Carbon-14, Cesium-131, Cesium-137, Chromium-51, Cobalt-57, Cobalt-58, Cobalt-60, Dysprosium-165, Erbium-169, Fluorine-18, Gallium-67, Gallium-68, Gold-198, Hydrogen-3, Indium-111, Indium-113m, Iodine-123, Iodine-125, Iodine-131 Diagnostic, Iodine-131 Therapeutic, Iridium-192, Iron-59, Iron-82, Krypton-81m, Lanthanum-140, Lutetium-177, Molybdenum-99, Nitrogen-13, Oxygen-15, Paladium-103, Phosphorus-32, Radon-222, Radium-224, Rhenium-186, Rhenium-188, Rb-82, Samarium-153, Selenium-75, Sodium-22, Sodium-24, Strontium-89, Thallium-201, Xenon-127, Xenon-133, Yttrium-90, and combinations, and mixtures thereof.

Where combinations of radioisotopes are used with the microparticles or combinations of MAS microparticles with other microparticles are used to obtain a combination of radioisotopes, preferred combinations of radioisotopes include having one or more beta emitters along with one or more gamma emitters. Examples include but are not limited to Y-90/In-111, Y-90/Tc-99m, P-32/In-111 P-32/Tc-99m, Ho-166/In-111, Ho-166/Tc-99m, Sm-53/In-111 and Sm-153/Tc-99m.

Particularly preferred radioisotopes include Indium-111 (radiodiagnostic gamma emitters), Lutetium-177 (being both a beta and gamma emitter), and Samarium-153 and Yttrium-90 (radiotherapeutic beta emitters). Radioisotopes have been used for imaging and function studies of the brain, myocardium, thyroid, lungs, liver, gallbladder, kidneys, bone, blood, and tumors. Indium-111 pentetreotide has been used in imaging of neuroendocrine tumors that overexpress somatostatin receptors and has become standard for localization of these tumors. This radioligand is internalized into the cell and can induce receptor-specific cytotoxicity by emission of Auger electrons. Lutetium-177 having both gamma and beta properties enables its use in imaging as well as treatment. It has a shorter radius of penetration that Y-90 which makes it an ideal candidate for radiotherapy of small tumors. Samarium-153 lexidronam (chemical name Samarium-153-ethylene diamine tetramethylene phosphonate, abbreviated Samarium-153 EDTMP, trade name Quadramet) is a complex of a radioisotope of the lanthanide element samarium with the chelator EDTMP. It has been used to treat cancer pain when cancer has spread to the bone. Once injected into a vein, it distributes throughout the body and localizes in areas where cancer has invaded the bone, allowing the beta panicles (electrons) to destroy the nearby cancer cells. It is also commonly used in lung cancer, prostate cancer, breast cancer, and osteosarcoma. Yttrium-90 has been used in the treatment of various cancers including lymphoma, leukemia, ovarian, colorectal, pancreatic, and bone cancers, and in treatment of rheumatoid arthritis by radionuclide synovectomy.

Although an attempt is made to provide an exhaustive list, it is well-known to nuclear medicine specialists that radioisotopes may be produced using a generator system, a thermal neutron reactor, a cyclotron, or fission produced. Accordingly, any radioisotopes with functional equivalents to those listed are intended to be encompassed wherever appropriate within the scope of the present invention.

Tailoring Radioactivity

The radiation dosage delivered through the use of the neutron activated microparticles upon administration to the patient can be varied by controlling the number of microparticles administered and by controlling the amount of radiation emitting isotope contained by the microparticles. The amount of radiation emitting radioisotope contained by the microparticles is affected by two factors: the amount of the neutron activatable isotope that will be converted to a radioisotope by irradiation, and the length of time of irradiation.

Types of Cancers

The microparticles of the present invention may be used in a variety of clinical situations, including but not limited to: selective internal radiation therapy for tumors of areas that have favorable vasculature, including the liver, spleen, brain, kidney, head & neck, uterine, and prostate. The microparticles may also be used for imaging, including a Liver/Spleen Scan—for tumors, cysts or hepatocellular disease; a Brain Scan—for tumors, trauma, or dementia; a Tumor Scan for malignant tumors or metastatic disease of the Kidney, Head & Neck, Uterine/Gynecological; and any Scan or Therapy having favorable vasculature for this approach.

One radionuclide imaging technique contemplated as within the scope of the invention is single photon emission computed tomography (SPECT).

Since most organs, besides the liver, have only one blood vessel that feeds it, administration may be performed by delivery to that main feeder artery and allowing the microparticles to lodge in the capillary bed since they are too large to move through the capillary. The liver may require a specialized delivery regimen, as exemplified below. In another embodiment, the vessel that feeds the tumor may be identified, and this artery is used to deliver the microparticles.

Delivery

The microspheres may be administered to the patient through the use of catheters either alone or in combination with vasoconstricting agents or by any other means of administration that effectively causes the microspheres to become embedded in the cancerous or tumor bearing tissue. For purposes of administration, the microspheres are preferably suspended in a medium that has a sufficient density or viscosity that prevents the microspheres from settling out of suspension during the administration procedure. Presently preferred liquid vehicles for suspension of the microspheres include polyvinylpyrrolidone (PVP), sold under the trade designation Plasdone K-30 and Povidone by GAF Corp, a contrast media sold under the trade designation Metrizamide by Nyegard & Co. of Oslo, Norway, a contrast media sold under the trade designation Renografin 76 by E. R. Squibb & Co., 50% dextrose solutions and saline.

Treatment and/or Imaging of Liver Cancer

The microspheres of the present invention may be used in the treatment and/or imaging of liver cancer by introducing a catheter into the hepatic artery and administering the radioactive microspheres. Preferably, the microspheres are suspended in a medium such as Plasdone K-30 or Metrizamide for purposes of administration. The particle density in the liver after administration is preferably optimized for treatment, imaging or both, depending on the medical isotope used. When administered in this manner, the microspheres become embedded in the capillary bed of the tumorous liver tissue rather than in normal liver, thereby delivering the radiation dosage primarily to the tumor. Vasoconstricting drugs may additionally be used to decrease hepatic artery flow to normal liver. Microspheres used in this treatment preferably comprise Y-90 because of their short-ranged radiation.

Throughout this text, the term "therapy" and/or treatment means any effect which mitigates any damage or any medical disorder, to any extent, and includes treatment of damage itself as well as the control of damage. The term "treatment" means any amelioration of disorder, disease, syndrome, condition, pain or a combination of one or more thereof. Treatment of cancer refers to killing cancer cells.

Radioactivity

In accordance with a preferred embodiment, glass microspheres having a specific composition may have an activity of about 0.2 to about 0.6 Ci/gm of glass after irradiation. To achieve the desired level of activity, the microspheres are irradiated for an effective period. For instance, microspheres comprising about 40% by weight $Y_2O_3$ are irradiated in a nuclear reactor to a level of about 3 Ci/gm which requires about 75 hours of irradiation at $1 \times 10^{14}$ neutrons/$cm^2$ sec. Thus, by activating the microspheres to a level above the preferred administration range, decay of activity of the activated microspheres may occur during processing and shipment prior to administration to the patient and still permit administration within the preferred range of activity. If a glass microsphere containing Y-90 were used for the treatment of liver cancer, the specific activity required through irradiation would provide a half-life of 64 hours for Y-90, which defines the decay during transit and the time it remains active in the body.

The following non-limiting example(s) merely helps to further illustrate the invention.

EXAMPLE 1

A. Microsphere Preparation

The glass compositions were prepared from reagent grade chemicals. Batches yielding 50 grams of glass were melted in platinum crucibles in an electric furnace at an appropriate temperature. A typical melting cycle required three hours for batch additions at 1000 degree C. (aluminosilicate) to 1500 degree C. (MAS glass) and three to four hours to refine the melt at the approximate melting temperature. The crucible containing the melt was quenched in 25.degree. C. water, after which the resultant glass fit was broken from the crucible and ground to –100 mesh. The –100 mesh glass powder was then slowly fed by a vibrating spatula into an oxygen/propane flame where surface tension pulled the molten particles into spheres. The flow rates of oxygen and propane were adjusted for each glass composition so as to yield the highest fraction of spherical particles. After spheroidizing, the microspheres were wet screened with deionized water, rinsed in acetone and dried.

As various changes could be made in the above methods and products, without departing from the scope of the invention, it is intended that all matter contained in the above description or shown in any accompanying drawings shall be interpreted as illustrative and not in a limiting sense.

Any references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A radioactive low density microparticle for radioimaging or radiation therapy of a mammal comprising a biologically compatible magnesium-alumina-silicate glass microparticle having a density of about 3.0 g/cc or less said microparticle containing at least one beta or gamma radiation emitting isotope distributed substantially throughout the magnesium-alumina-silicate glass which emits a therapeutic intensity and amount of beta or gamma radiation, and a balance of elements selected from the group consisting of elements that do not become radioactive upon neutron irradiation and elements that have a half-life that is sufficiently short so that the elements do not emit a significant amount of beta or gamma radiation at the time of administration, the microparticle having a chemical durability such that subsequent to administration of the microparticle to the mammal, the microparticle will not release a significant amount of the radiation emitting radioisotope into the mammal's system;

wherein the glass microparticle comprises 8-14 wt % MgO, 32-35 wt % $Al_2O_3$, and 47-52 wt % $SiO_2$.

2. The radioactive low density microparticle of claim 1, wherein the isotope is at least one medical isotope selected from the group consisting of Samarium-153, Yttrium-90, and Lutetium-177.

3. The radioactive low density microparticle of claim 1, wherein the isotope is a combination of Samarium-153 and Yttrium-90.

4. The radioactive low density microparticle of claim 1, wherein the density is about 2.8 g/cc or less.

5. The radioactive low density microparticle of claim 1, wherein the isotope is $^{90}Y$ (Yttrium-90) and has specific activity of 162 mCi per $10^7$ microparticles for therapy.

6. The radioactive low density microparticle of claim 5, further comprising a second radiation emitting isotope consisting of $^{177}Lu$ (Lutetium-177), wherein the $^{177}Lu$ has specific activity of 32 mCi per $10^7$ microparticles for imaging.

7. The radioactive low density microparticle of claim 5, further comprising a second radiation emitting isotope consisting of $^{153}Sm$ (Samarium-153), wherein the $^{153}Sm$ has a specific activity of 12 mCi per 250,000 microparticles for imaging.

8. A method of administering radioactive magnesium-alumina-silicate glass microparticles to a patient in need thereof, comprising delivering by catheter to an artery that feeds an organ or a tumor of a patient a composition comprising the radioactive low density microparticles of claim 1, and a physiologically acceptable carrier.

9. The method of claim 8, further comprising wherein the isotope is a combination of samarium-153 and yttrium-90.

10. The method of claim 8, further comprising wherein the isotope is lutetium-177.

11. The method of claim 8, further comprising wherein the isotope is samarium-153.

12. The method of claim 8, wherein the organ or tumor is selected from the group consisting of liver, spleen, brain, kidney, head & neck, uterine, and prostate.

13. A method of obtaining a radiologic image of a patient's organ, comprising administering by catheter to an artery that feeds an organ of a patient a composition containing radioactive magnesium-alumina-silicate glass microparticles that contain samarium-153 or lutetium-177 as the medical isotope in a physiologically acceptable carrier, and obtaining the radiologic image of the patient's organ by capturing the radiation emitted by the samarium-153 or lutetium-177 using a suitable radionuclide imaging technique;

wherein the glass microparticles comprise 8-14 wt % MgO, 32-35 wt % $Al_2O_3$, 47-52 wt % $SiO_2$, and said samarium-153 or lutetium-177.

14. The method of claim 13, further comprising wherein the radionuclide imaging technique is single photon emission computed tomography (SPECT).

15. The method of claim 13, wherein the organ or tumor is selected from the group consisting of liver, spleen, brain, kidney, head & neck, uterine, and prostate.

16. A method of administering radioactive magnesium-alumina-silicate glass microparticles that contain both samarium-153 as a radiodiagnostic medical isotope and yttrium-90 as a radiotherapeutic medical isotope to a patient in need thereof, comprising delivering by catheter to the hepatic artery of a patient a composition comprising radioactive magnesium-alumina-silicate glass microparticles that contain a radiodiagnostic amount of samarium-153 and a radiotherapeutic amount of yttrium-90, and a physiologically acceptable carrier;
wherein the glass microparticles comprise 8-14 wt % MgO, 32-35 wt % $Al_2O_3$, 47-52 wt % $SiO_2$, the radiodiagnostic amount of samarium-153, and the radiotherapeutic amount of yttrium-90.

17. The radioactive low density microsphere of claim 1 wherein the glass microparticle comprises the 8-14 wt % MgO, 32-35 wt % $Al_2O_3$, the 47-52 wt % $SiO_2$ and one of a) Lu-177, b) Y-90, c) Sm-153, d) Lu-153+Y-90, or e)Sm-153+Y 90, as said at least one beta or gamma radiation emitting isotope.

18. The radioactive low density microsphere of claim 17 wherein the glass microparticle consists essentially of the 8-14 wt % MgO, the 32-35 wt % $Al_2O_3$, the 47-52 wt % $SiO_2$ and the one of a) Lu-177, b) Y-90, c)Sm-153, d) Lu-153+Y-90, or e) Sm-153+Y 90 as said at least one beta or gamma radiation emitting isotope.

19. The method of claim 16 wherein the magnesium-alumina-silicate glass microparticles are about 20 to about 200 um in diameter.

20. The method of claim 16 wherein the magnesium-alumina-silicate glass microparticles are about 5 to about 75 um in diameter.

21. The method of claim 16 wherein the magnesium-alumina-silicate glass microparticles are about 20 to about 40 um in diameter.

22. The radioactive low density microparticle of claim 1, wherein the microparticle is melt-derived from a mixture of particles comprising MgO, $Al_2O_3$, $SiO_2$ and an oxide of the radiation-emitting isotope.

* * * * *